United States Patent [19]

Ghilardi et al.

[11] 3,981,676

[45] Sept. 21, 1976

[54] LYOPHILIZED DYES AND THE USE THEREOF TO COLOR KERATINIC FIBERS

[75] Inventors: Giuliana Ghilardi, Paris; Pierre Bore, Montfermeil; Jean-Francois Grollier, Paris, all of France

[73] Assignee: L'Oreal, Paris, France

[22] Filed: June 25, 1973

[21] Appl. No.: 372,933

Related U.S. Application Data

[63] Continuation-in-part of Ser. No. 120,353, March 2, 1971, abandoned.

[30] Foreign Application Priority Data

| Mar. 3, 1970 | Luxemburg | 60449 |
| Oct. 19, 1970 | Luxemburg | 61890 |
| Feb. 15, 1971 | Luxemburg | 62596 |
| June 26, 1972 | Luxemburg | 65589 |

[52] U.S. Cl. ................................. 8/10; 8/10.1; 8/10.2; 8/11; 8/25; 8/32; 8/79; 8/93
[51] Int. Cl.² ........................................ A61K 7/12
[58] Field of Search ............ 8/10, 11, 79, 85, 89, 8/10.1, 10.2, 93; 260/396 R, 396 N

[56] References Cited

UNITED STATES PATENTS

| 2,077,887 | 4/1937 | Kranzlein et al. | 260/28 |
| 2,134,505 | 10/1938 | Brunner et al. | 260/246 |
| 2,267,741 | 12/1941 | Langbein | 260/315 |
| 2,693,467 | 11/1954 | Anderau et al. | 260/246 |
| 3,336,155 | 8/1967 | Rowe | 8/79 |
| 3,402,986 | 9/1968 | Zviak et al. | 8/10 |
| 3,583,877 | 6/1971 | Rosenblum et al. | 8/79 |
| 3,681,403 | 8/1972 | Somlo et al. | 260/396 R |
| 3,698,852 | 10/1972 | Pantzer et al. | 8/10.2 |
| 3,712,790 | 1/1973 | Kalopissis et al. | 8/11 |
| 3,730,677 | 5/1973 | Kalopissis et al. | 8/11 |
| 3,758,268 | 9/1973 | Kalopissis et al. | 8/11 |
| 3,787,174 | 1/1974 | Kalopissis et al. | 8/11 |
| 3,824,074 | 7/1974 | Bugaut et al | 8/10 |
| 3,867,094 | 2/1975 | Kalopissis et al. | 8/10 |
| 3,876,368 | 4/1975 | Kalopissis et al. | 8/10 |
| 3,884,625 | 5/1975 | Kalopissis et al. | 8/10 |
| 3,899,288 | 8/1975 | Galerne | 8/10.2 |
| 3,905,761 | 9/1975 | Kalopissis et al. | 8/10.2 |
| 3,929,403 | 12/1975 | Kalopissis et al. | 8/10.1 |

FOREIGN PATENTS OR APPLICATIONS

| 1,526,397 | 6/1968 | France | 8/10.2 |
| 1,492,121 | 5/1969 | Germany | 8/11 |
| 826,479 | 1/1960 | United Kingdom | 8/10.1 |
| 807,089 | 1/1959 | United Kingdom | 8/79 |

OTHER PUBLICATIONS

P—Benzoquinonediimine—A Vital Intermediate in Oxidative Hair Dyeing, J. F. Corbett, J. Soc. Cosmetic Chemists, vol. 20, No. 4, pp. 253–263, (Apr. 1969).

*Primary Examiner*—Benjamin R. Padgett
*Assistant Examiner*—T. S. Gron
*Attorney, Agent, or Firm*—Cushman, Darby & Cushman

[57] ABSTRACT

A dye for coloring hair is one of an indamine, indoaniline, indophenol, diaminobenzoquinone or mixtures thereof which is lyophilized from a solution of the dye in an organic solvent or in an aqueous solution of the organic solvent by freezing the solution at a temperature of −200° to −60°C, and then subliming the frozen solution under a vacuum at a temperature lower than the melting point of the frozen solution. The thus lyophilized dye can be desorped to eliminate, if necessary, residual moisture. The lyophilized dye can be solubilized in an aqueous solution to produce a hair dye composition and can be present therein in amounts of about 0.0005–4 percent by weight of said composition.

9 Claims, No Drawings

LYOPHILIZED DYES AND THE USE THEREOF TO COLOR KERATINIC FIBERS

This application is a continuation-in-part of our application Ser. No. 120,353, filed Mar. 2, 1971, now abandoned.

The present invention relates to lyophilized dyes, to a process for preparing the same and to their use in dye compositions for dyeing human hair.

It has been known, heretofore, that there are two modes of dyeing keratinic fibers which differ from each other by the nature of the dyes used in each and by the result which each achieves: i.e. either a permanent dyeing or a non-permanent dyeing of the fibers. A permanent dyeing which is generally characterized by very good fastness to washing and resistance to several shampooings is ordinarily effected with the aid of dyes called oxidation dyes, i.e. uncolored compounds which develop a coloration in situ, under the action of an oxidizing agent. A non-permanent dyeing, although generally not exhibiting comparable fastness to washing characteristics, nonetheless can be advantageous in that it provides easy modification of the color of the hair and is ordinarily effected with the aid of dyes called direct dyes such as azo dyes, anthraquinone dyes or aromatic nitro derivatives. However, the direct dyes used until now to effect a non-permanent dyeing exhibited the disadvantage of producing colorations which lack desirable transparency or glints, and thus is not considered as aesthetic as the dyeing obtainable using an oxidation dye.

Further, the art also recognizes that the use of certain dyes of the family of indoanilines, indamines and indophenols, has not enjoyed the degree of commercialization as would be desired, due in a large measure to instability of these dyes in solution.

In order to improve the stability of these dyes, the applicants have heretofore provided them in the anhydrous solid state, notably in the form of a powder which is solubilized in an appropriate vehicle immediately before its application to the hair. In this manner, the stability of the indamines, indoanilines and indophenols has been increased thereby providing the art with a hair dyeing process having the advantages it had formerly sought.

Notwithstanding it was observed that some difficulty persisted with regard to the solubility of said dye in powder form in the dye composition vehicle. It has been observed that the dissolution or dispersion of the same is not as complete or as rapid as is desired especially when it is required that dye compositions containing these powdered dyes be produced immediately before their application to the hair.

The applicants have now found that this difficulty can be overcome and that a dye of the family of indamines, indophenols and indoanilines in the form of stable powders which can be rapidly and completely solubilizd in cosmetic vehicles so as to form a dye composition for immediate application to the hair, can be produced by lyophilizing a solution of said dye isolated from its reaction mixture in an organic solvent thereof or an aqueous solution of said solvent.

Accordingly, one object of the present invention is the provision of a process for preparing lyophilized dyes comprising lyophilizing one or more isolated dyes belonging to the class of indamines, indoanilines, indophenols and diamino benzoquinones or mixtures thereof, in solution in one or more organic solvent or an aqueous mixtue of said solvent by freezing said solution and sublimating said frozen solution by heating the same under a vacuum at a temperature lower than the melting point of said frozen solution to provide a lyophilized dye. Optionally, the lyophilized dye can be subjected to a desorption operation to eliminate any residual moisture content of the lyophilized dye.

The indamines, indoanilines and indophenols employed in the lyophilization process of the present invention can be a compound of the formula

$$Y - Ar_1 - N = Ar_2 = X \qquad (I)$$

or a corresponding tautomeric form thereof, wherein $Ar_1$ and $Ar_2$; each independently represent an aromatic hydrocarbon or heterocyclic nucleus, each optionally substituted by one or more electron donor groups such as amino, hydroxy, lower alkoxy, lower alkyl, acylamino or a halogen such as chlorine or bromine; Y represents hydroxy or

wherein $R_1$ and $R_2$ each independently represent hydrogen, lower alkyl: hydroxy lower alkyl, or amino lower alkyl with the amine function optionally being substituted or acylated; and X represents oxygen, imine or iminium; or the salt of these compounds.

It is convenient to note that the nomenclature adopted for these compounds corresponds to a numbering of the aromatic rings $Ar_1$ and $Ar_2$ which is as follows:

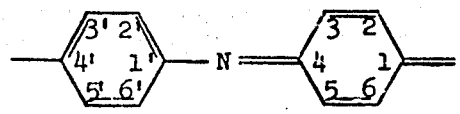

Representative indamines usefully employed in the process of the present invention include:

N-[(4'-dimethylamino)phenyl]-3-amino-6-methyl benzoquinone diimine;

N-[(4'-amino-2'-methoxy-5'-methyl)phenyl]-2-azo-3-amino benzoquinonediimine monoacetate;

the double chloride of zinc and N-[(ethyl β-acetylaminoethyl)-4'-amino phenyl]-3-amino-6-methoxy benzoquinone diimine;

N-[(4'-amino-2'-methoxy-5'-methyl)phenyl]-3-amino-6-methyl benzoquinone diimine monoacetate;

the double chloride of zinc and N-[(ethyl β-acetylaminoethyl)-4'-amino phenyl]-3-hydroxy benzoquinoneimine N', N'-diethyliminium The process of the present invention is also applicable to the lyophilization of particular indamines of said formula (I) wherein $Ar_1$ is a 7'-naphthyl-(6'-hydroxy-1'-oxa-4'-aza-1',2',3',4'-tetrahydro)ring. The said indamines, referred to as phenomorpholines, are, for example, N-[(6'-hydroxy-1'-oxa-4'-aza-1',2',3',4'-tetrahydro)-7'-naphthyl]-3-methoxy benzoquinonediimine and N-[(6'-hydroxy-1'-oxa-4'-aza-1',2',3',4'-tetrahydro)-7'-naphthyl]-2-methyl-5-methoxy benzoquinonediimine.

Representative indoanilines usefully employed in the process of the present invention include:

N-[(4'-amino-2'-methoxy-3',5'-dimethyl)phenyl]-2,6-dimethyl benzoquinoneimine,
N-[(4'-amino-phenyl]-3-acetylamino-6-methyl benzoquinoneimine,
N-[(4'-amino)phenyl]-3-acetylamino-2,6-dimethyl benzoquinoneimine,
N-[(4'-dimethylamino)phenyl]-3-acetylamino-6-methyl benzoquinoneimine,
N-[(4'-amino-2'-methoxy-5'-methyl)phenyl]-3-acetylamino-6-methyl benzoquinoneimine,
N-[(4'-amino-2'-methoxy)phenyl]-3-acetylamino-6-methyl benzoquinoneimine, and
N-[(4'-amino-3',5'-dimethyl)phenyl]-3-acetylamino-6-methyl benzoquinoneimine.

Representative indophenols usefully employed in the process of the present invention include:
N-[(4'-hydroxy-6'-chloro)phenyl]-2,6-dimethyl benzoquinoneimine,
N-[(4'-hydroxy)phenyl]-3-acetylamino-6-methyl benzoquinoneimine,
N-[(4'-hydroxy-3',5'-dimethyl)phenyl]-2,6-dimethyl benzoquinoneimine,
N-[(4'-hydroxy)-phenyl]-2,5-dimethyl benzoquinoneimine,
N-[(4'-hydroxy-2',6'-dimethyl)phenyl]-2,6-dimethyl benzoquinoneimine,
N-[(4'-hydroxy)phenyl]-2,3-dimethyl benzoquinoneimine,
N-[(4'-hydroxy)phenyl]-2,6-dimethyl benzoquinoneimine, and
N-[(4'-hydroxy)phenyl]-3-amino-6-methyl benzoquinoneimine.

Representative diamino-benzoquinones usefully employed in the process of the present invention can include 2,5-diamino-1,4-benzoquinones of the formula

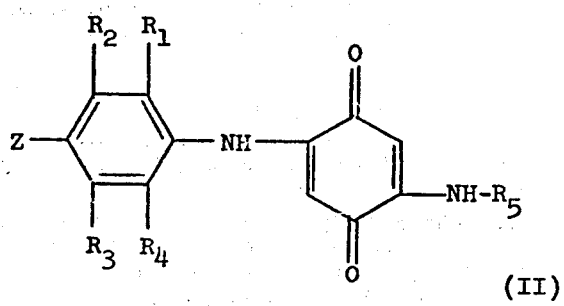

(II)

wherein $R_1$, $R_2$, $R_3$ and $R_4$, each independently represent hydrogen, a halogen such as chlorine or bromine, lower alkyl or lower alkoxy; $R_5$ represents hydrogen, lower alkyl, lower alkyl substituted by one or more hydroxy groups, or an amino-alkyl of the formula

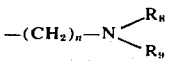

wherein $n$ is 2–6 and $R_8$ and $R_9$ each independently represent hydrogen, lower alkyl, lower alkyl substituted by one or more hydroxy groups, or acylamino, $R_8$ and $R_9$ also being able to form, together with the nitrogen atom to which they are attached, a six membered heterocycle such as piperidinyl or morpholinyl; and Z represents hydroxy or

wherein $R_6$ and $R_7$ each independently represent hydrogen, lower alkyl, lower alkyl substituted by one or more hydroxy groups, acylamino, mesylamino, or aminoalkyl of the formula

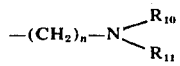

wherein $n$ is 2–6, $R_{10}$ and $R_{11}$ each independently represent lower alkyl, lower alkyl substituted by one or more hydroxy groups, or acylamino, $R_{10}$ and $R_{11}$ also being able to form, together with the nitrogen atom to which they are attached, a six membered heterocycle such as piperidinyl and morpholinyl.

Representative diamino-benzoquinones usefully employed in the present invention include 2-amino-5-[(N-ethyl, N-β-piperidinoethyl)-4'-amino-anilino]-1,4-benzoquinone.

In the above definitions the terms lower alkyl and lower alkoxy means those having 1–4 carbon atoms while the term acyl includes an aliphatic residue having 2–5 carbon atoms.

In another embodiment of the present invention salts of the compounds of formula II with a mineral or organic acid can also be lyophilized. Representative mineral or organic salts of these compounds include the hydrochloride, hydrobromide, sulfate, acetate, lactate and citrate thereof, as well as the quaternary ammonium salts thereof in those instances where the dye molecule includes a quaternizable tertiary amine group. Obviously other acids conventionally employed to produce salts used in cosmetic preparations can also be utilized.

The lyophilization process can be carried out with a variety of organic solvents to assure the complete solubilization of the dyes and the attainment of a homogeneous solution for use in the lyophilization operation. Representative organic solvents usefully employed include tertiobutyl alcohol, benzyl alcohol, dimethylsulfoxide, dioxane and their mixtures as well as aqueous mixtures of said organic solvents.

The solution submitted to lyophilization can also contain as fillers, oligopeptides, such as hydrolysis products of proteins, amino acids, hydroxyethyl cellulose, hydroxy methyl cellulose or polymers such as polyvinylpyrrolidone (PVP) having a molecular weight ranging between 40,000 to 360,000, the preferred molecular weight being 40,000, or copolymers such as the copolymer of vinylpyrrolidone and vinyl acetate (MW = 40,000–160,000 ) 70%:30% to 30%:70%, the preferred proportion being 60%:40%, having a viscosity of 3.3 to 4 cp in a 5% solution in ethanol at a temperature of 25°C, or copolymers of crotonic acid and vinyl acetate, 90%:10% having a molecular weight of 40,000 to 200,000 and preferably 50,000 and a viscosity of 7 to 9 cp in a 5% solution of tetrachloroethane at a temperature of 35°C. The addition of these fillers has the effect of increasing the total volume and ensuring a very high degree of reproducibility of the characteristics of the lyophilizate obtained and of its dyeing properties. Generally, the total amount of filler employed will range between 1 to 20 and preferably about 5 weight percent of the solution to be lyophilized.

Representative protein hydrolysis products include such products as those known under the commercial designations "Keratin Hydrolyzate" by GEO; "Complex Aminoacid" by GEO; "Casein Hydrolyzate" by GEO; "Capilane KS" by "Sandoz" "Polypeptide Wilson WSP250" and "Polypetide LSN" by Stepan Chemicals.

Representative amino acids that can be employed include alanine, glycine, glutamic acid and cystine.

In carrying out the process of the present invention, lyophilization is effected, preferably, by freezing the solution of said dye in said organic solvent at a temperature of about −200°C to −60°C, generally at a temperature of about −70°C or lower. The sublimation stage of the lyophilization operation is carried out at a pressure equal to or lower than 0.1 mm Hg generally about 0.01 mm Hg to 0.1 mm Hg by using, for example, an apparatus commercially known as "USIFROID SMJ" which is provided with an internal condenser. It will be appreciated however that any conventional freeze-drying means can be employed. Sublimation is generally effected at a temperature of about −50°C to −30°C and generally at a temperature of about −45°C or lower.

Desorption of the lyophilized product can be carried out in the same apparatus used to sublime the same at a temperature generally between 15° and 60°C under a very low pressure, generally in the order of about 10 mm Hg. to 0.001 mm Hg and preferably about 0.01 mm Hg, the temperature of the condenser ordinarily being maintained at about −70°C or lower. The total time of lyophilization and desorption under these conditions is generally of the order of about 20 hours although shorter or longer times can be employed. There is thus obtained a lyophilized product in the form of a powder having a very high specific surface area.

Another embodiment of the present invention relates to lyophilized dyes produced in accordance with the above defined lyophilization process.

Still another object of the present invention relates to powdered dyes which can be dissolved in a cosmetic vehicle to produce a dye composition for application to human hair.

The said powdered dyes can include, in addition to the lyophilized dye, cosmetic resins, optical brightening agents and/or components conventionally employed in cosmetic compositions such as thickening agents, surfactants and/or other dyes such as acid, basic or direct dyes, for instance, anthraquinone dyes, azo dyes, nitro dyes, complex metalliferous dyes and/or other indamines, indoanilines, indophenols or diamino benzoquinones.

The powdered dyes can also be provided in the form of tablets or pills.

Moreover, the dye can be present in said powdered dyes in the form of microencapsulated or coated particles.

Still another object of the present invention relates to dye compositions obtained by dissolving or dispersing the above defined powdered dyes in a cosmetic vehicle comprising an aqueous solution.

The concentration of the indamines, indoanilines, indophenols or diaminobenzoquinones in the dye composition can be extremely slight because of the great dyeing power of these compounds. This concentration varies generally between about 0.0005–4 percent by weight of said composition.

The said aqueous solution serving as a cosmetic vehicle can be simply water to which can be added, optionally, a suitable amount of a mineral or organic base, such as triethanolamine or ammonia, or a suitable amount of an acidic component such as lactic acid or citric acid, so as to adjust the final pH of the composition to a value between, preferably, about 3–10. Obviously other pH adjusting agents conventionally employed in cosmetic preparations can also be employed. The said aqueous solution can also include one or more low molecular weight alcohols, such as ethanol or isopropanol or one or more dye adjuvants such as butyl glycol or benzyl alcohol, surfactants, solar filters such as benzylidene camphor, optical brightening agents, antioxidants such as butylhydroxyanisole and/or components conventionally employed in capillary cosmetic formulations such as thickening agents, wetting agents, swelling agents, penetrating agents or perfumes.

The said aqueous solution can also include, in addition to said alcohol, one or more cosmetic resins such as polyvinylpyrrolidone having a molecular weight ranging from 40,000 to 360,000, a copolymer of vinylpyrrolidone and vinyl acetate having a molecular weight ranging from 40,000 to 160,000 (70%:30% to 30%:70%, respectively), a copolymer of crotonic acid and vinyl acetate (90:10) having a molecular weight ranging from 40,000 to 200,000 and mixtures thereof. Obviously, other conventional cosmetic film forming resins can also be employed. Generally, the cosmetic resin is employed in amounts of about 1 to 3 percent by weight of the total composition. In this embodiment, the dye composition which is prepared just before use on the hair, comprises a colored hair setting lotion.

The dye compositions of this invention can also be provided in the form of an aqueous or hydroalcoholic solution, gel or cream. In producing the hydroalcoholic solution there is generally employed a lower alkanol such as ethanol or isopropanol present in amounts of about 1 to 96 weight percent of the resulting aqueous alkanol solution. The dye compositions of this invention can also be packaged in an aerosol container, a dosage bottle or in a container for several components which are admixed just prior to use.

The process of dyeing hair in accordance with the present invention is effected preferably by a simple application of the dye composition obtained by admixing the powdered dye with an aqueous solution, followed by rolling the hair upon curlers and/or drying the hair, without rinsing or washing prior to rolling the hair on curlers or drying it. However, in another embodiment of this process, it is possible to precede the rolling up on curlers or drying operations with a washing or rinsing operation.

The dye compositions prepared from the lyophilizates or composite powders containing the lyophilizate as well as other components and/or other dyes exhibit as an important advantage the reproducibility of the dyes obtained on hair.

Moreover, the coloration achieved can be easily varied since it is possible in accordance with the present invention to easily modify the concentration of the lyophilized dye in the composition and also to modify the composition containing the said lyophilized dye by including therein various mixtures of dyes proportioned according to the effect ultimately desired, without being concerned about the instability of the dye and other unfavorable phenomenon heretofore observed with dyes of the same family but present in the form heretofore employed.

Finally, as already mentioned above, the fundamental advantage of a rapid and complete solubilization of the lyophilized powdered dyes characterizes the present invention and permits the easy preparation of dye compositions immediately before their application to the hair.

In the following examples which illustrate the invention, comparative data relating to the solubility of the lyophilized powdered dyes of this invention with respect to corresponding powdered non-lyophilized dyes of the same chemical nature but simply sieved or ground are provided (Examples 15 to 28).

EXAMPLE 1

The following solution is prepared:

| | |
|---|---|
| N-[(4'-hydroxy-6'-chloro)phenyl]-2, 6-dimethyl benzoquinone-imine | 1 g |
| Polyvinylpyrrolidone (MW = 40,000) | 2 g |
| Tertiobutylalcohol, q.s.p. | 100 cc |

This solution is lyophilized by freezing the same at a temperature of −60°C and then subliming it at a pressure of about 0.1 mm Hg at a temperature of −40°C for 12 hours, after which it is subjected to a desorption operation at a pressure of about 0.01 mm Hg and at a temperature of 35°C for 8 hours thereby producing the desired lyophilized dye.

EXAMPLE 2

The following solution is prepared:

| | |
|---|---|
| N-[(4'-hydroxy)phenyl]-3-acetylamino-6-methyl benzoquinoneimine | 1 g |
| Copolymer of vinylpyrrolidone-vinyl-acetate (60/40); viscosity in 5% ethanol = 3.3–4 cps | 1 g |
| Dioxane | 75 cc |
| Water, q.s.p. | 100 cc |

The said solution is lyophilized by freezing at a temperature of −60°C and then subliming it at a pressure of about 0.01 mm Hg and at a temperature of −40°C for 12 hours, after which it is subjected to a desorption operation at a pressure of about 0.01 mm Hg and thereby providing at 25°C for 8 hours the desired lyophilized dye.

EXAMPLE 3

The following solution is prepared:

| | |
|---|---|
| N-[(4'-amino-2'-methoxy-3',5'-dimethyl) phenyl]-2,6-dimethyl benzoquinone-imine | 1 g |
| Tertiobutyl alcohol | 50 cc |
| Water, q.s.p. | 100 cc |

This solution is lyophilized by freezing at a temperature of −60°C and then subliming it at a pressure of about 0.05 mm Hg and at a temperature of −40°C for 12 hours, after which it is subjected to a desorption operation at a pressure of about 0.01 mm Hg for 12 hours at 30°C to provide the desired lyophilized dye.

EXAMPLE 4

The following solution is prepared:

| | |
|---|---|
| N-[(4'-amino)phenyl]-3-acetylamino-6-methyl benzoquinoneimine | 0.66 g |
| Copolymer of vinylpyrrolidone-vinyl acetate (as in Example 2) | 3.75 g |
| Dioxane | 85 cc |
| Water, q.s.p. | 100 cc |

The solution is lyophilized by freezing it at a temperature of −70°C and then subliming it at a pressure of about 0.1 mm Hg and at −35°C for 12 hours, followed by desorption for 8 consecutive hours at a pressure of about 0.01 mm Hg at 30°C to provide the desired lyophilized dye.

EXAMPLE 5

The following solution is prepared:

| | |
|---|---|
| N-[(4'-hydroxy)phenyl]-3-acetylamino-2,6-dimethyl benzoquinone-imine | 1 g |
| Copolymer of vinylpyrrolidone-vinyl acetate (as in Example 2) | 4 g |
| Dimethylsulfoxide | 1 cc |
| Water | 9 cc |
| Dioxane, q.s.p. | 100 cc |

This solution is lyophilized by freezing it at a temperature of −70°C, then subliming it at a temperature of −45°C and at a pressure of about 0.1 mm Hg to provide the desired lyophilized dye.

EXAMPLE 6

The following solution is prepared:

| | |
|---|---|
| N-[(4'-amino)phenyl]-3-acetylamino-2,6-dimethyl benzoquinone-imine | 1 g |
| Copolymer of vinylpyrrolidone-vinyl acetate (as in Example 2) | 4 g |
| Dimethylsulfoxide | 1 cc |
| Water | 9 cc |
| Dioxane, q.s.p. | 100 cc |

The solution is lyophilized by freezing it at a temperature of −60°C, then subliming it at a temperature of −45°C and at a pressure of about 0.05 mm Hg for about 12 hours, followed by desorption for 8 hours at a pressure of about 0.01 mm Hg at 30°C, thereby providing the desired lyophillized dye.

EXAMPLE 7

The following solution is prepared:

| | |
|---|---|
| N-[(4'-dimethylamino)phenyl]-3-acetylamino-6-methyl benzoquinoneimine | 1 g |
| Copolymer of vinylpyrrolidone-vinyl acetate (as in Example 2) | 4 g |
| Dimethylsulfoxide | 1 cc |
| Water | 9 cc |
| Dioxane, q.s.p. | 100 cc |

This solution is lyophilized by freezing it at a temperature of −70°C, then subliming it at a temperature of −45°C and at a pressure of about 0.1 mm Hg for 12 hours, followed by desorption at a pressure of about 0.01 mm Hg at 30°C for 8 hours to provide the desired lyophilized dye.

EXAMPLE 8

The following solution is prepared:

| | |
|---|---|
| N-[(4'-dimethylamino)phenyl]-3-acetylamino-6-methyl benzoquinoneimine | 0.06 g |
| N-[4'-amino)phenyl]-3-acetylamino-2,6-dimethyl benzoquinoneimine | 0.09 g |
| N-[(4'-hydroxy)phenyl]-3-acetylamino-2,6-dimethyl benzoquinoneimine | 0.2 g |
| Copolymer of vinylpyrrolidone-vinyl acetate (as in Example 2) | 4.65 g |
| Dimethylsulfoxide | 1 cc |
| Water | 10 cc |
| Dioxane, q.s.p. | 100 cc |

This solution is lyophilized by freezing it at a temperature of −60°C, then subliming it at a temperature of −35°C and at a pressure of about 0.01 mm Hg for 12 hours, followed by desorption for 12 hours at 25°C and at a pressure of about 0.1 mm Hg to produce the desired lyophilizate of a mixture of dyes.

EXAMPLE 9

The following solution is prepared:

| | |
|---|---|
| N-[(4'-amino-2'-methoxy-5'-methyl)phenyl]-3-acetylamino-6-methyl benzoquinoneimine | 0.5 g |
| Dioxane | 90 cc |
| Copolymer of vinylpyrrolidone-vinyl acetate (as in Example 22) | 2.5 g |
| Water, q.s.p. | 100 cc |

The solution is lyophilized by freezing it at a temperature of −60°C, then subliming it at a temperature of −35°C and at a pressure of about 0.1 mm Hg for 12 hours, followed by desorption for 8 hours at 20°C and at a pressure of about 0.01 mm Hg to produce the desired lyophilized dye.

EXAMPLE 10

The following solution is prepared:

| | |
|---|---|
| N-[(4'-amino-2'-methoxy)phenyl]-3-acetylamino-6-methyl benzoquinoneimine | 0.5 g |
| Copolymer of vinylpyrrolidone-vinyl acetate (as in Example 2) | 2.5 g |
| Dioxane | 90 cc |
| Water, q.s.p. | 100 cc |

This solution is lyophilized by freezing it at a temperature of −60°C, then subliming it at a temperature of −35°C and at a pressure of about 0.01 mm Hg for 7 hours, followed by desorption for 8 hours at 25°C and at a pressure of about 0.01 mm Hg to produce the desired lyophilized dye.

EXAMPLE 11

The following solution is prepared:

| | |
|---|---|
| N-[(4'-amino-3',5'-dimethyl)phenyl]-3-acetylamino-6-methyl benzoquinoneimine | 1 g |
| Dimethylsulfoxide | 1 g |
| Copolymer of vinylpyrrolidone-vinyl acetate (as in Example 2) | 4 g |
| Water | 10 cc |
| Dioxane, q.s.p. | 100 cc |

This solution is lyophilized by freezing it at a temperature of −60°C, then subliming it at a temperature of −45°C and at a pressure of about 0.05 mm Hg for 12 hours, followed by desorption for 8 hours at 25°C and at a pressure of about 0.01 mm Hg to provide the desired lyophilized dye.

EXAMPLE 12

The following solution is prepared:

| | |
|---|---|
| N-[(6'-hydroxy-1'-oxa-4'-aza-1',2',3',4'-tetrahydro) 7'-naphthyl]-3-methoxy benzoquinonediimine | 4 g |
| Dimethylsulfoxide | 10 cc |
| Dioxane | 79 cc |
| Benzyl alcohol | 1 cc |
| Water, q.s.p. | 100 cc |

This solution is lyophilized by freezing it at a temperature of −70°C, then subliming it at a temperature of −45°C and at a pressure of about 0.1 mm Hg to produce the desired lyophilized dye.

EXAMPLE 13

The following solution is prepared:

| | |
|---|---|
| N-[(6'-hydroxy-1'-oxa-4'-aza-1',2',3',4'-tetrahydro) 7'-naphthyl]-2-methyl-5-methoxy benzoquinonediimine | 4 g |
| Copolymer of vinylpyrrolidone-vinyl acetate (as in Example 2) | 4 g |
| Dimethylsulfoxide | 1 cc |
| Dioxane | 89 cc |
| Water, q.s.p. | 100 cc |

This solution is lyophilized by freezing it at a temperature of −70°C and then subliming it at a temperature of about −45°C and at a pressure of about 0.01 mm Hg to produce the desired lyophilized dye.

EXAMPLE 14

The following solution is prepared:

| | |
|---|---|
| N-[(4'-hydroxy-6'-chloro)phenyl-2,6- | |

-continued

| dimethyl benzoquinoneimine | 4 g |
| --- | --- |
| 2-amino-5-[(N-ethyl,N-β-piperidinoethyl)-4'-amino anilino]-1,4-benzoquinone | 2 g |
| Dioxane | 20 cc |
| Dimethylsulfoxide | 100 cc |

This solution is lyophilized by freezing it at a temperature of −70°C, then subliming it at a temperature of −45°C and at a pressure of about 0.1 mm Hg to provide the desired lyophilizate of a mixture of dyes.

EXAMPLE 15

A hair dye composition is prepared by mixing together, at the moment of use, 0.100 g of powder $P_1$ and 25 cc of solution $S_1$, defined below.

| Powder $P_1$: | Lyophilized dye of Example 1 | |
| --- | --- | --- |
| Solution $S_1$: | | |
| | Copolymer of vinylpyrrolidone-vinyl acetate (60/40) viscosity in a 5% solution of ethanol = 3.3 – 4 cps | 2.0 g |
| | Ethyl alcohol | 50 cc |
| | Triethanolamine, q.s.p. | pH 7 |
| | Water, q.s.p. | 100 cc |

This composition is applied to chestnut colored hair. After setting and drying, the hair exhibits particularly aesthetic mahogany glints.

SOLUBILITY COMPARISON 0.100 g of powder $P_1$ is completely solubilized within 15 seconds in 25 cc of solution $S_1$ while the same quantity of the same dye employed in Example 1 but passed only through a sieve, No. 80 (ASTM standard), is only 84 percent solubilized under the same conditions in the same solution.

EXAMPLE 16

A hair dye composition is prepared by admixing at the moment of use 0.100 g of powder $P_2$ and 25 g of solution $S_2$, defined below.

| Powder $P_2$: | Lyophilized dye of Example 2 | |
| --- | --- | --- |
| Solution $S_2$: | | |
| | Copolymer of crotonic acid - vinyl acetate (90:10) MW = 50,000 | 2.5 g |
| | Ethyl alcohol | 50 cc |
| | Triethanolamine, q.s.p. | pH 8 |
| | Benzylidene camphor | 0.2 g |
| | Water, q.s.p. | 100 cc |

This dye composition when applied as a hair setting lotion to natural light chestnut colored hair imparted thereto, after setting and drying, particularly luminous and pretty pearly golden glints.

SOLUBILITY COMPARISON 0.100 g of powder $P_2$ is completely solubilized within 15 seconds in 25 cc of solution $S_2$ while the same quantity of a mixture of the same dye and copolymer passed only through a sieve, No. 80 (ASTM standard), left 77 percent insolubles under the same conditions in the same solution.

EXAMPLE 17

A hair dye composition is prepared by admixing at the moment of use 0.025 g of powder $P_3$ and 25 cc of solution $S_3$ defined below.

| Powder $P_3$: | Lyophilized dye of Example 3 | |
| --- | --- | --- |
| Solution $S_3$: | | |
| | Copolymer of vinylpyrrolidone-vinyl acetate (60/40) viscosity in a 5% solution of ethanol = 3.3 – 4 cps | 2.0 g |
| | Ethyl alcohol | 50 cc |
| | Triethanolamine, q.s.p. | pH 6.5 |
| | Water, q.s.p. | 100 cc |

This hair dye composition when applied as a hair setting lotion on natural black hair, after setting and drying, imparts thereto particularly luminous and pretty bluish glints.

SOLUBILITY COMPARISON 0.025 g of powder $P_3$ is completely solubilized within 15 seconds in 25 cc of solution $S_3$ whereas the same quantity of the same dye of Example 3 but passed only through a sieve, No. 80 (ASTM standard), left 52 percent insolubles under the same conditions in the same solution.

EXAMPLE 18

A hair dye composition is prepared by admixing at the moment of use 0.100 g of powder $P_4$ and 25 cc of solution $S_4$, defined below.

| Powder $P_4$: | Lyophilized dye of Example 4 | |
| --- | --- | --- |
| Solution $S_4$: | | |
| | Copolymer of vinylpyrrolidone-vinyl acetate (70:30) MW = 40,000 | 2.0 g |
| | Ethyl alcohol | 50 cc |
| | N-acetylethanolamine | 0.15 g |
| | Benzylidene camphor | 0.2 g |
| | Triethanolamine, q.s.p. | pH 7 |
| | Water, q.s.p. | 100 cc |

This hair dye composition when applied as a hair setting lotion to natural light chestnut colored hair, after setting and drying, imparts thereto very aesthetic and pretty ash violet glints.

SOLUBILITY COMPARISON 0.100 g of powder $P_4$ is completely solubilized with 15 seconds in 25 cc of solution $S_4$ whereas the same quantity of dye of Example 4 but passed only through a sieve, No. 100 (ASTM standard), left 31 percent insolubles under the same conditions in the same solution.

EXAMPLE 19

A hair dye composition is prepared by admixing at the moment of use 0.100 g of powder $P_5$ and 25 cc of solution $S_5$, defined below.

| Powder $P_5$: | Lyophilized dye of Example 5 | |
| --- | --- | --- |
| Solution $S_5$: | | |
| | Copolymer of crotonic acid - vinyl acetate (90:10) MW = 50,000 | 2.0 g |
| | Ethyl alcohol | 50 cc |

| | |
|---|---|
| Triethanolamine, q.s.p. | pH 9 |
| Water, q.s.p. | 100 cc |

This hair dye composition when applied as a hair setting lotion to golden chestnut colored hair, after setting and drying, imparts thereto very aesthetic and pretty pearly golden glints.

SOLUBILITY COMPARISON 0.100 g of powder $P_5$ is completely solubilized within 15 seconds in 25 cc of solution $S_5$ whereas the same quantity of dye of Example 4 but passed only through a sieve, No. 100 (ASTM standard), left 42 percent insolubles under the same conditions in the same solution.

EXAMPLE 20

A hair dye composition is prepared at the moment of use by admixing 0.020 g of powder $P_6$ and 25 cc of solution $S_6$, defined below.

| Powder $P_6$: | | |
|---|---|---|
| | Lyophilized dye of Example 6 | |
| Solution $S_6$: | | |
| | Hydroxyethylcellulose, sold under the tradename "Natrosol 250L" | 0.5 g |
| | Ethyl alcohol | 30 cc |
| | Citric acid, q.s.p. | pH 5 |
| | Water, q.s.p. | 100 cc |

This hair dye comparison when applied as a hair rinse on blond hair after drying imparts thereto particularly aesthetic and pretty pearly ashen glints.

SOLUBILITY COMPARISON 0.100 g of powder $P_6$ is completely solubilized within 15 seconds in 25 cc of solution $S_6$ whereas the same quantity of the dye of Example 6 but passed only through a sieve, No. 80 (ASTM standard), left 41 percent insolubles under the same conditions in the same solution.

EXAMPLE 21

A hair dye composition is prepared at the moment of use by admixing 0.005 g of powder $P_7$ and 25 cc of solution $S_7$, defined below.

| Powder $P_7$: | | |
|---|---|---|
| | Lyophilized dye of Example 7 | |
| Solution $S_7$: | | |
| | Copolymer of crotonic acid-vinyl acetate (90:10) MW = 50,000 | 1.5 g |
| | Copolymer of vinylpyrrolidone-vinyl acetate (60:40) viscosity in 5% ethanol solution = 3.3 – 4 cps | 0.5 g |
| | Ethyl alcohol | 50 cc |
| | Triethanolamine, q.s.p. | pH 7 |
| | Water, q.s.p. | 100 cc |

This hair dye composition when applied as a hair setting lotion to bleached hair, after setting and drying, imparted thereto a very light ash blond coloration.

SOLUBILITY COMPARISON 0.100 g of powder $P_7$ is completely solubilized within 15 seconds, with agitation, in 25 cc of solution $S_7$ whereas the same quantity of the dye of Example 7 but passed only through a sieve, No. 100 (ASTM standard), left 86 percent insolubles under the same conditions in the same solution.

EXAMPLE 22

A hair dye composition is prepared at the moment of use by admixing 0.100 g of powder $P_8$ and 25 cc of solution $S_8$, defined below.

| Powder $P_8$: | | |
|---|---|---|
| | Lyophilized mixture of dyes of Example 8 | |
| Solution $S_8$: | | |
| | Copolymer of crotonic acid - vinyl acetate (90:10) MW = 50,000 | 200 g |
| | Ethyl alcohol | 50 cc |
| | Triethanolamine, q.s.p. | pH 7 |
| | Water, q.s.p. | 100 cc |

This hair dye composition when applied as a hair setting lotion to blond hair, after setting and drying, imparted thereto a very aesthetic and very pretty pearly ash blond coloration.

SOLUBILITY COMPARISON 0.100 g of powder $P_8$ is completely solubilized within 15 seconds in 25 cc of solution $S_8$ whereas the same quantity of the mixture of dyes of Example 8 but passed only through a sieve, No. 80 (ASTM standard), is only 50 percent soluble under the same conditions in the same solution.

EXAMPLE 23

A hair dye composition is prepared at the moment of use by admixing 0.150 g of powder $P_9$ and 25 cc of solution $S_9$, defined below.

| Powder $P_9$: | | |
|---|---|---|
| | Lyophilized dye of Example 9 | |
| Solution $S_9$: | | |
| | Copolymer of vinylpyrrolidone-vinyl acetate (60:40) viscosity in a 5% ethanol solution = 3.3 – 4 cps | 2.0 g |
| | Ethyl alcohol | 45 cc |
| | Triethanolamine, q.s.p. | pH 7 |
| | Water, q.s.p. | 100 cc |

This hair dye composition when applied as a hair setting lotion to naturally deep chestnut colored hair imparts thereto, after drying, pleasing blue violet glints.

SOLUBILITY COMPARISON 0.150 g of powder $P_9$ is completely solubilized within 15 seconds in 25 cc of solution $S_9$ whereas the same quantity of the dye of Example 9 but only powdered in a "Forplex" grinder, left 52 percent insoluble under the same conditions in the same solution.

EXAMPLE 24

A hair dye composition is prepared at the moment of use by admixing 0.050 g of powder $P_{10}$ and 25 cc of a solution $S_{10}$ defined below.

| Powder $P_{10}$: | |
|---|---|
| | Lyophilized dye of Example 10 |
| Solution $S_{10}$: | |
| | Copolymer of vinylpyrrolidone - |

-continued

| | |
|---|---|
| vinyl acetate (60:40) viscosity in a 5% ethanol solution = 3.3 – 4 cps | 2.0 g |
| Ethyl alcohol | 50 cc |
| Benzylidene camphor | 0.2 g |
| Butylhydroxy anisole | 0.1 g |
| Citric acid, q.s.p. | pH 5 |
| Water, q.s.p. | 100 cc |

This hair dye composition when applied as a hair setting lotion to blond hair imparted thereto, after setting and drying, a very aesthetic pearly ash blond coloration.

SOLUBILITY COMPARISON 0.150 g of powder $P_{10}$ is completely solubilized within 15 seconds in 25 cc of solution $S_{10}$ whereas the same quantity of the dye of Example 10, but only powdered in a "Forplex 00" grinder, left 25 percent insolubles under the same conditions in the same solution.

EXAMPLE 25

A hair dye composition is prepared at the moment of use by admixing 0.100 g of powder $P_{11}$ and 25 cc of solution $S_{11}$ defined below.

| | |
|---|---|
| Powder $P_{11}$: | Lyophilized dye of Example 11 |
| Solution $S_{11}$: | |
| Copolymer of vinylpyrrolidone - vinyl acetate (70:30) MW = 40,000 | 1.9 g |
| Ethyl alcohol | 50 cc |
| Triethanolamine, q.s.p. | pH 9 |
| Water, q.s.p. | 100 cc |

This hair dye composition when applied as a hair setting lotion to chestnut colored hair imparted thereto, after drying, a very aesthetic ashen chestnut coloration.

SOLUBILITY COMPARISON 0.100 g of powder $P_{11}$ is completely solubilized within 15 seconds in 25 cc of solution $S_{11}$ whereas the same quantity of the dye of Example 11 but passed only through a sieve, No. 80 (ASTM standard), left 35 percent insolubles under the same conditions in the same solution.

EXAMPLE 26

A hair dye composition is prepared at the moment of use by admixing 0.025 g of powder $P_{12}$ and 25 cc of solution $S_{12}$, defined below.

| | |
|---|---|
| Powder $P_{12}$: | Lyophilized dye of Example 12 |
| Solution $S_{12}$: | |
| Copolymer of vinylpyrrolidone - vinyl acetate (60:40) viscosity in 5% ethanol solution = 3.3 – 4 cps | 2.0 g |
| Ethyl alcohol | 50 cc |
| Triethanolamine, q.s.p. | pH 7 |
| Water, q.s.p. | 100 cc |

This hair dye composition when applied as a hair setting lotion to chestnut colored hair imparted thereto, after drying, very aesthetic and pretty green glints.

SOLUBILITY COMPARISON 0.025 g of powder $P_{12}$ are completely solubilized within 15 seconds in 25 cc of solution $S_{12}$ whereas the same quantity of the dye of Example 12 but passed only through a sieve, No. 80 (ASTM standard), was only 35 percent soluble under the same conditions in the same solution.

EXAMPLE 27

A hair dye composition is prepared at the moment of use by admixing 0.070 g of powder $P_{13}$ and 25 cc of solution $S_{13}$, defined below.

| | |
|---|---|
| Powder $P_{13}$: | Lyophilized dye of Example 13 |
| Solution $S_{13}$: | |
| Copolymer of crotonic acid - vinyl acetate (90:10) MW = 50,000 | 2.0 g |
| Ethyl alcohol | 40 cc |
| Triethanolamine, q.s.p. | pH 8.5 |
| Benzylidene camphor | 0.2 g |
| Water, q.s.p. | 100 cc |

This hair dye composition when applied as a hair setting lotion on bleached hair imparted thereto, after setting and drying, a very pretty green coloration.

SOLUBILITY COMPARISON 0.070 g of powder $P_{13}$ is completely solubilized within 15 seconds in 25 cc of solution $S_{13}$ whereas the same quantity of the dye of Example 13 but passed only through a sieve, No. 80 (ASTM standard), is only 50 percent soluble under the same conditions in the same solution.

EXAMPLE 28

A hair dye composition is prepared at the moment of use by admixing 0.040 g of powder $P_{14}$ and 25 cc of a solution $S_{14}$, defined below.

| | |
|---|---|
| Powder $P_{14}$: | Lyophilized dye of Example 14 |
| Solution $S_{14}$: | |
| Copolymer of vinylpyrrolidone - vinyl acetate (60:40) viscosity in a 5% ethanol solution = 3.3 – 4 cps | 2.0 g |
| Ethyl alcohol | 35 cc |
| Triethanolamine, q.s.p. | pH 7 |
| Water, q.s.p. | 100 cc |

This hair dye composition when applied as a hair setting lotion to light chestnut colored hair imparts thereto, after drying, very aesthetic pearly glints.

SOLUBILITY COMPARISON 0.040 g of powder $P_{14}$ is completely solubilized within 15 seconds in 25 cc of solution $S_{14}$ whereas the same quantity of dye of Example 15 but passed only through a sieve, No. 80 (ASTM standard), is only 35 percent soluble under the same conditions in the same solution.

EXAMPLE 29

A hair dye composition is prepared at the moment of use by admixing 0.025 g of a powder, the preparation of which is given below, with 25 cc of a solution, also defined below.

| Preparation of Powder | |
|---|---|
| The following solution is prepared: | |
| N-[(4'-amino-2'-methoxy-5'-methyl)phenyl]-2-aza-3-amino benzoquinonediimine | 1 g |
| Dioxane | 75 cc |
| Water, q.s.p. | 100 cc |

This solution is lyophilized by freezing it at a temperature of −60°C and then subliming it at a pressure of about 0.01 mm Hg and at a temperature of −40°C for 12 hours to produce the desired lyophilized dye.

| Solution | |
|---|---|
| Copolymer of crotonic acid - vinyl acetate (90:10) MW = 50,000 | 2.5 g |
| Triethanolamine, q.s.p. | pH 7 |
| Ethyl alcohol | 30 cc |
| Water, q.s.p. | 100 cc |

This hair dye composition when used as a hair setting lotion on chestnut colored hair imparts thereto particularly aesthetic and very pretty ashen glints.

SOLUBILITY COMPARISON 0.025 g of the above powder is completely solubilized within 30 seconds in 25 cc of the above solution, whereas the same quantity of the same dye used in preparing the powder but passed only through a sieve, No. 90 (ASTM standard), left 25 percent insolubles under the same conditions in the same solution.

EXAMPLE 30

A hair dye composition is prepared at the moment of use by admixing 0.100 g of a powder, the preparation of which is given below, with 25 cc of a solution, defined below,

| Preparation of Powder | |
|---|---|
| The following solution is prepared: | |
| N-[(3'-aza-2',4'-diamino)phenyl]-2,6-dimethyl benzoquinoneimine | 1 g |
| Polyvinylpyrrolidone (MW = 40,000) | 3 g |
| Dioxane | 70 cc |
| Water, q.s.p. | 100 cc |

This solution is lyophilized by freezing it at a temperature of −60°C and then subliming it at a pressure of 0.05 mm Hg and at a temperature of −40°C for 13 hours to produce the desired lyophilized dye.

| Solution | |
|---|---|
| Copolymer of crotonic acid - vinyl acetate (90:10) MW = 50,000 | 1.9 g |
| Triethanolamine, q.s.p. | pH 7.5 |
| Ethyl alcohol | 45 cc |
| Water, q.s.p. | 100 cc |

This hair dye composition when used as a hair setting lotion on chestnut colored hair imparts thereto particularly aesthetic and pretty ashen glints.

SOLUBILITY COMPARISON 0.100 g of the above powder is completely solubilized within 30 seconds in 25 cc of the above solution whereas the same quantity of the same dye used to prepare the powder but passed only through a sieve, No. 80 (ASTM standard), left 42 percent solids under the same conditions in the same solution.

EXAMPLE 31

A hair dye composition is prepared at the moment of use by admixing 0.100 g of a powder, the preparation of which is given below, with 25 cc of the solution also given below.

| Preparation of Powder | |
|---|---|
| The following solution is prepared: | |
| N-[(4'-hydroxy)phenyl]-3-amino-6-methyl benzoquinoneimine | 1 g |
| Copolymer of vinylpyrrolidone vinyl acetate (60:40) viscosity in a 5% ethanol solution = 3.3 - 4 cps | 3 g |
| Dioxane | 75 cc |
| Water, q.s.p. | 100 cc |

This solution is lyophilized by freezing it at a temperature of −60°C, subliming it at a pressure of 0.05 mm Hg and at a temperature of −40°C for 12 hours, followed by desorption for 8 hours at 25°C and at a pressure of 0.01 mm Hg to produce the desired lyophilized dye.

| Solution | |
|---|---|
| Copolymer of crotonic acid - vinyl acetate (90:10) MW = 50,000 | 1.8 g |
| Ethyl alcohol | 50 cc |
| Triethanolamine, q.s.p. | pH 8 |
| Water, q.s.p. | 100 cc |

This hair dye composition when applied as a hair setting lotion to natural chestnut colored hair imparts thereto pretty mahogany glints.

SOLUBILITY COMPARISON 0.100 g of the above powder is completely solubilized within 30 seconds in 25 cc of the above solution whereas the same quantity of a mixture of the same dye and polymer used to prepare the powder but passed only through a sieve, No. 80 (ASTM standard), left 70 percent insolubles under the same conditions in the same solution.

EXAMPLE 32

A hair dye composition is prepared at the moment of use by admixing 0.050 g of a powder, the preparation of which is given below, with 25 cc of the solution defined below.

| Preparation of Powder | |
|---|---|
| The following solution is prepared: | |
| N-[(4'-hydroxy)phenyl]-3-amino-6-methyl benzoquinoneimine | 4 g |
| Copolymer of vinylpyrrolidone - vinyl acetate (60:40) viscosity in a 5% ethanol solution = 3.3 - 4 cps | 10 g |
| Dimethylsulfoxide | 20 g |

-continued

| | |
|---|---|
| Dioxane, q.s.p. | 100 cc |

This solution is lyophilized by freezing it at a temperature of −60°C and then subliming it at a pressure of 0.01 mm Hg and at a temperature of −45°C for 18 hours to produce the desired lyophilized dye.

| Solution | |
|---|---|
| Copolymer of crotonic acid -  vinyl acetate (90:10)  MW = 50,000 | 2.0 g |
| Ethyl alcohol | 30 cc |
| Triethanolamine, q.s.p. | pH 8 |
| Water, q.s.p. | 100 cc |

This hair dye composition when applied as a hair setting lotion to blond hair imparts thereto particularly luminous and very pretty golden glints.

SOLUBILITY COMPARISON 0.050 g of the above powder is completely solubilized within 30 seconds in 25 cc of the above solution whereas the same quantity of the dye and polymer used to prepare the powder but passed only through a sieve, No. 80 (ASTM standard), left 34 percent insolubles under the same conditions in the same solution.

EXAMPLE 33

A hair dye composition is prepared at the moment of use by admixing 0.020 g of a powder, the preparation of which is given below, with 25 cc of the solution defined below.

| Preparation of Powder | |
|---|---|
| The following solution is prepared: | |
| N-[(4′-dimethylamino)phenyl]-3-amino-  6-methyl benzoquinonediimine  hydrochloride | 1 g |
| The double chloride of zinc and N-[(4′-  ethyl, acetylamino ethyl amino)  phenyl]-3-amino-6-methoxy benzo-  quinonediimine | 0.5 g |
| Dioxane | 75 cc |
| Water, q.s.p. | 100 cc |

This solution is lyophilized by freezing it at a temperature of −60°C and subliming it at a pressure of about 0.1 mm Hg and at a temperature of −45°C to provide the desired lyophilized dye.

| Solution | |
|---|---|
| Copolymer of crotonic acid -  vinyl acetate (90:10)  MW = 50,000 | 2.0 g |
| Triethanolamine, q.s.p | pH 8.5 |
| Ethyl alcohol | 50 cc |
| Water, q.s.p. | 100 cc |

This hair dye composition when applied as a hair setting lotion to brown hair imparts thereto particularly aesthetic and very pretty bluish glints.

SOLUBILITY COMPARISON 0.020 g of the above powder is completely solubilized within 30 seconds in 25 cc of the above solution whereas the same quantity of the same mixture of dyes used to prepare this powder but passed only through a sieve, No. 80 (ASTM standard), left 15 percent insolubles under the same conditions in the same solution.

EXAMPLE 34

A hair dye composition is prepared at the moment of use by admixing 0.100 g of a powder, the preparation of which is given below, with 25 cc of the solution defined below.

| Preparation of Powder | |
|---|---|
| The following solution is prepared: | |
| N-[(4′-amino-2′-methoxy-5′-methyl)  phenyl]-3-amino-6-methyl  benzoquinoneimine monoacetate | 1 g |
| The double chloride of zinc and  N-[(ethyl, β-acetylaminoethyl) 4-  amino phenyl]-3-hydroxy benzo-  quinoneimine N,N-diethyliminium | 0.2 g |
| Copolymer of vinylpyrrolidone -  vinyl acetate (60:40)  viscosity in 5% ethanol  solution = 3.3 − 4 cps | 10 g |
| Dioxane | 75 cc |
| Water, q.s.p. | 100 cc |

This solution is lyophilized by freezing it at a temperature of −60°C and then subliming it at a pressure of 0.05 mm Hg and at a temperature of −45°C to provide the desired lyophilized dye.

| Solution | |
|---|---|
| Copolymer of crotonic acid -  vinyl acetate (90:10)  MW = 50,000 | 2.2 g |
| Triethanolamine, q.s.p. | pH 6.5 |
| Ethyl alcohol | 50 cc |
| Water, q.s.p. | 100 cc |

This hair dye composition when applied as a hair setting lotion to natural chestnut colored hair imparts thereto particularly aesthetic and very pretty ashen glints.

SOLUBILITY COMPARISON 0.100 g of the above powder is completely solubilized within 30 seconds in 25 cc of the above solution whereas the same quantity of the mixture of dyes used to prepare the powder but passed only through a sieve, No. 80 (ASTM standard), left 53 percent insolubles under the same conditions in the same solution.

EXAMPLE 35

A hair dye composition is prepared at the moment of use by admixing 0.050 g of a powder, the preparation of which is given below, with 25 cc of a solution defined below.

| Preparation of Powder | |
|---|---|
| The following solution is prepared: | |
| 2-β-hydroxyethylamino-5-[(N-di-β-  hydroxy-ethyl) 4′-amino  anilino]-1,4-benzoquinone | 4 g |
| Copolymer of vinylpyrrolidone -  vinyl acetate (60:40)  viscosity in 5% ethanol  solution = 3.3 − 4 cps | 10 g |
| Dimethylsulfoxide | 20 cc |
| Dioxane, q.s.p. | 100 cc |

This solution is lyophilized by freezing it at a temperature of −60°C and subliming it at a pressure of 0.1 mm Hg and at a temperature of −45°C for 13 hours to provide the desired lyophilized dye.

| Solution | |
|---|---|
| Copolymer of crotonic acid - vinyl acetate (90:10) MW = 50,000 | 1.5 g |
| Triethanolamine, q.s.p. | pH 8 |
| Ethyl alcohol | 30 cc |
| Water, q.s.p. | 100 cc |

This hair dye composition when applied as a hair setting lotion to deep chestnut colored hair imparts thereto particularly aesthetic and a very pretty green glints.

SOLUBILITY COMPARISON 0.050 g of the above powder is completely solubilized within 30 seconds in 25 cc of the above solution whereas the same quantity of the dye used to prepare the powder but passed only through a sieve, No. 80 (ASTM standard), left 51 percent insolubles under the same conditions in the same solution.

EXAMPLE 36

A hair dye composition is prepared at the moment of use by admixing 0.100 g of a powder, the preparation of which is given below, with 25 cc of a solution defined below.

| Preparation of Powder | |
|---|---|
| The following solution is prepared: | |
| N-[(4'-hydroxy)phenyl]-3-acetylamino-6-methyl benzoquinoneimine | 1 g |
| Polypeptide LSN sold by Stepan Chemicals | 1 g |
| Dioxane | 65 cc |
| Water, q.s.p. | 100 cc |

This solution is lyophilized by freezing it at a temperature of −60°C, then subliming it at a pressure of 0.01 mm Hg and at a temperature of −40°C for 12 hours, followed by desorption at 25°C and at a pressure of about 0.01 mm Hg for 8 hours to produce the desired lyophilized dye.

| Solution | |
|---|---|
| Copolymer of crotonic acid - vinyl acetate (10:90) MW = 50,000 | 2.5 g |
| Ethyl alcohol | 50 cc |
| Triethanolamine, q.s.p. | pH 8 |
| Benzylidene camphor | 0.2 g |
| Water, q.s.p. | 100 cc |

This hair dye composition when applied as a hair setting lotion to natural light chestnut colored hair imparts thereto, after setting and drying, particularly luminous and very pretty pearly golden glints.

SOLUBILITY COMPARISON 0.100 g of the above powder is completely solubilized within 15 seconds in 25 cc of the above solution whereas the same quantity of dye used to prepare the powder but passed only through a sieve, No. 80 (ASTM standard), left 77 percent insolubles under the same conditions in the same solution.

EXAMPLE 37

A hair dye composition is prepared at the moment of use by admixing 0.100 g of a powder, the preparation of which is given below, with 25 cc of a solution defined below.

| Preparation of Powder | |
|---|---|
| N-[(4'-dimethylamino)phenyl]-3-acetylamino-6-methyl benzoquinoneimine | 0.06 g |
| N-[(4'-amino)phenyl]-3-acetylamino-4,6-dimethyl benzoquinoneimine | 0.09 g |
| N-[(4'-hydroxy)phenyl]-3-acetylamino-2,6-dimethyl benzoquinoneimine | 0.2 g |
| Alanine | 0.5 g |
| Water | 25 cc |
| Dioxane, q.s.p. | 100 cc |

This solution is lyophilized by freezing it at a temperature of −60°C, then subliming it at a pressure of 0.1 mm Hg and at a temperature of −35°C for 12 hours, followed by desorption for 12 hours at 25°C and at a pressure of about 0.01 mm Hg to produce the desired lyophilized dye.

| Solution | |
|---|---|
| Copolymer of crotonic acid - vinyl acetate (90:10) MW = 50,000 | 2.0 g |
| Ethyl alcohol | 50 cc |
| Triethanolamine, q.s.p. | pH 7 |
| Water, q.s.p. | 100 cc |

This hair dye composition when applied as a hair setting lotion to blond hair imparts thereto, after drying, a very aesthetic and pretty pearly ash blond coloration.

SOLUBILITY COMPARISON 0.100 g of the above powder is completely solubilized within 15 seconds in 25 cc of the above solution whereas the same quantity of the mixtures of dyes used to prepare the powder but passed only through a sieve, No. 80 (ASTM standard), is only 50 percent soluble under the same conditions in the same solution.

EXAMPLE 38

A hair dye composition is prepared at the moment of use by admixing 0.150 g of a powder, the preparation of which is given below, with 25 cc of a solution defined below.

| Preparation of Powder | |
|---|---|
| The following solution is prepared: | |
| N-[(4'-amino-2'-methoxy-5'-methyl)phenyl]-3-acetylamino-6-methyl benzoquinoneimine | 0.5 g |
| Dioxane | 50 cc |
| Glycocoll | 1 g |
| Water, q.s.p. | 100 cc |

This solution is lyophilized by freezing it at a temperature of −60°C, then subliming it at a pressure of 0.01 mm Hg and at a temperature of −35°C for 12 hours, followed by desorption at 20°C and at a pressure of about 0.01 mm Hg for 8 hours to produce the desired lyophilized dye.

| Solution |  |
|---|---|
| Copolymer of vinylpyrrolidone - vinyl acetate (60:40) viscosity in a 5% ethanol solution = 3.3 – 4 cps | 2.0 g |
| Ethyl alcohol | 45 cc |
| Triethanolamine, q.s.p. | pH 7 |
| Water, q.s.p. | 100 cc |

This hair dye composition when applied as a hair setting lotion to natural deep chestnut colored hair imparts thereto splendid blue violet glints.

SOLUBILITY COMPARISON 0.150 g of the above powder is completely solubilized within 15 seconds in 25 cc of the above solution whereas the same quantity of the same dye used to prepare the powder but powdered only in a Forplex grinder, left 52 percent insolubles under the same conditions in the same solution.

What is claimed is:

1. A process for preparing a lyophilized dye composition for coloring hair comprising freezing at a temperature of about −200° to −60°C a solution consisting essentially of, in an organic solvent or an aqueous solution of said organic solvent wherein said organic solvent is selected from the group consisting of dioxane, dimethyl sulfoxide, tert-butyl alcohol and a mixture thereof, a dye selected from the group consisting of a. a dye having the formula $Y - Ar_1 - N = Ar_2 = X$ or a corresponding tautomeric form thereof, wherein $Ar_1$ and $Ar_2$ each independently represents a member selected from the group consisting of phenyl, pyridyl and phenomorpholine, each optionally substituted by an electron donor group selected from the group consisting of amino, hydroxy, alkoxy having 1–4 carbon atoms, alkyl having 1–4 carbon atoms, acetylamino and halogen, Y is selected from the group consisting of hydroxy and

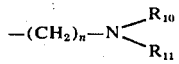

wherein $R_1$ and $R_2$ each independently represents a member selected from the group consisting of hydrogen, alkyl having 1–4 carbon atoms and acetylaminoalkyl wherein the alkyl moiety has 1–4 carbon atoms, and X represents a member selected from the group consisting of oxygen, imine and iminium;

b. a salt of (a) above; and
   c. 2,5-diamino-1,4-benzoquinone of the formula:

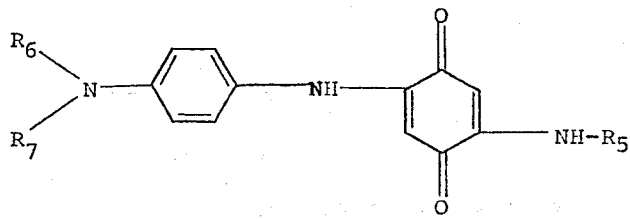

wherein $R_5$ represents a member selected from the group consisting of hydrogen and hydroxyalkyl having 1–4 carbon atoms, and $R_6$ and $R_7$ each independently represents a member selected from the group consisting of alkyl having 1–4 carbon atoms, hydroxyalkyl having 1–4 carbon atoms and aminoalkyl of the formula

wherein $n$ is 2–6 and $R_{10}$ and $R_{11}$ together with the nitrogen atom to which they are attached from a piperidinyl group. and subliming said frozen solution by heating the same under a vacuum to a temperature lower than the melting point of said frozen solution.

2. The process of claim 1 wherein said dye is selected from the group consisting of:

N-[(4′-hydroxy-6′-chloro)phenyl]-2,6-dimethyl benzoquinoneimine;
N-[(4′-hydroxy)phenyl]-3-acetylamino-6-methyl benzoquinoneimine;
N-[(4′-amino-2′-methoxy-3′,5′-dimethyl)phenyl]-2,6-dimethyl benzoquinoneimine;
N-[(4′-amino)phenyl]-3-acetylamino-6-methyl benzoquinoneimine;
N-[(4′-hydroxy)phenyl]-3-acetylamino-2,6-dimethyl benzoquinoneimine;
N-[(4′-amino)phenyl]-3-acetylamino-2,6-dimethyl benzoquinoneimine;
N-[(4′-dimethylamino)phenyl]-3-acetylamino-6-methyl benzoquinoneimine;
N-[(4′-amino-2′-methoxy-5′-methyl)phenyl]-3-acetylamino-6-methyl benzoquinoneimine;
N-[(4′-amino-2′-methoxy)phenyl]-3-acetylamino-6-methyl benzoquinoneimine;
N-[(4′-amino-3′,5′-dimethyl)phenyl]-3-acetylamino-6-methyl benzoquinoneimine;
N-[(4′-hydroxy-3′,5′-dimethyl)phenyl]-2,6-dimethyl benzoquinoneimine;
N-[(4′-hydroxy)phenyl]-2,5-dimethyl benzoquinoneimine;
N-[(4′-hydroxy-2′,6′-dimethyl)phenyl]-2,6-dimethyl benzoquinoneimine;
N-[(4′-hydroxy)phenyl]-2,3-dimethyl benzoquinoneimine;
N-[(4′-hydroxy)phenyl]-2,6-dimethyl benzoquinoneimine;
N-[(4′-hydroxy)phenyl]-3-amino-6-methyl benzoquinoneimine;
N-[(4′-dimethylamino)phenyl]-3-amino-6-methyl benzoquinonediimine;
N-[(4′-amino-2′-methoxy-5′-methyl)phenyl]-2-aza-3-amino benzoquinonediimine monoacetate;

the double chloride of zinc and N-[(ethyl, β-acetylaminoethyl)-4'-amino phenyl]-3-amino-6-methoxy benzoquinonediimine;

N-[(4'-amino-2'-methoxy-5'-methyl)phenyl]-3-amino-6-methyl benzoquinonediimine monoacetate; and the double chloride of zinc and N-[(ethyl β-acetylamino)-4'-amino phenyl]-3-hydroxy benzoquinoneimine N', N'-diethyliminium.

3. The process of claim 1 wherein said dye is selected from the group consisting of N-[(6'-hydroxy-1'-oxa-4'-aza-1', 2', 3', 4'-tetrahydro)-7'-naphthyl]-3-methoxy benzoquinonediimine and N-[(6'-hydroxy-1'-oxa-4'-aza-1', 2', 3', 4'-tetrahydro)-7'-naphthyl]-2-methyl-5-methoxy benzoquinonediimine.

4. The process of claim 1 wherein said dye is 2-amino5-[(N-ethyl, N-β-piperidinoethyl)-4'-amino anilino]-1,4-benzoquinone.

5. The process of claim 1 wherein said solution to be lyophilized also includes a filler selected from the group consisting of polyvinylpyrrolidone, copolymer of vinylpyrrolidone and vinyl acetate, copolymer of crotonic acid and vinyl acetate, an oligopeptide, alanine and glycocoll in an amount of about 1-20 percent by weight of said solution to be lyophilized.

6. The process of claim 1 which also includes, subsequent to subliming the frozen solution, desorbing the sublimate at a temperature between 15° and 60°C and at a pressure up to about 0.01 mm Hg.

7. The lyophilized dye composition made in accordance with the process of claim 1.

8. A process for preparing a lyophilized dye composition for coloring hair comprising freezing at a temperature of about −200° to −60°C a solution consisting essentially of, in an organic solvent or an aqueous solution of said organic solvent wherein said organic solvent is selected from the group consisting of dioxane, dimethyl sulfoxide, tert-butyl alcohol and a mixture thereof, a dye selected from the group consisting of N-[(4'-hydroxy-6'-chloro)phenyl]-2,6-dimethyl benzoquinoneimine, N-[(4'-hydroxy)phenyl]-3-acetylamino-6-methyl benzoquinoneimine, N-[(4'-amino-2'-methoxy-3',5'-dimethyl)phenyl]-2,6-dimethyl benzoquinoneimine. N-[(4'-amino)-phenyl]-3-acetylamino-6-methyl benzoquinoneimine, N-[(4'-hydroxy)phenyl]-3-acetylamino-2,6-dimethyl benzoquinoneimine, N-[(4'-amino)phenyl]-3-acetylamino-2,6-dimethyl benzoquinoneimine, N-[(4'-dimethylamino)phenyl]-3-acetylamino-6-methyl benzoquinoneimine, N-[(4'-amino-2'-methoxy-5'-methyl)phenyl]-3-acetylamino-6-methyl benzoquinoneimine, N-[(4'-amino-2'-methoxy)phenyl]-3-acetylamino-6-methyl benzoquinoneimine, N-[(4'-amino-3',5'-dimethyl)phenyl]-3-acetylamino-6-methyl benzoquinoneimine, N-[(6'-hydroxy-1'-oxa-4'-aza-1', 2', 3', 4'-tetrahydro) 7'-naphthyl]-3-methoxy benzoquinonediimine, N-[(6'-hydroxy-1'-oxa-4'-aza-1', 2', 3', 4'-tetrahydro) 7'-naphthyl]-2-methyl-5-methoxy benzoquinonediimine, 2-amino-5-[(N-ethyl, N-β-piperidinoethyl)-4'-amino anilino]-1,4-benzoquinone, N-[(4'-amino-2'-methoxy-5'-methyl)phenyl]-2-aza-3-amino benzoquinonediimine, N-[(3'-aza-2', 4'-diamino)phenyl]-2,6-dimethyl dbenzoquinoneimine, N-[(4'-hydroxy)phenyl]-3-amino-6-methyl benzoquinoneimine, N-[(4'-dimethylamino)phenyl[-3-amino-6-methyl benzoquinonediimine hydrochloride, the double chloride of zinc and N-[(4'-ethyl, acetylamino ethyl amino)phenyl]-3-amino-6-methoxy benzoquinonediimine, N-[(4'-amino-2'-methoxy-5'-methyl)phenyl]-3-amino-6-methyl benzoquinoneimine monoacetate, the double chloride of zinc and N-[(ethyl, β-acetylaminoethyl)-4'-amino phenyl]-3-hydroxy benzoquinoneimine N',N-diethyliminium, 2-β-hydroxyethylamino-5-[N-di-β-hydroxyethyl)-4'-amino anilino]-1,4-benzoquinone and a mixture thereof and subliming said frozen solution by heating the same under a vacuum to a temperature lower lower than the melting point of said frozen solution.

9. The lyophilized dye composition made in accordance with the process of claim 8.

* * * * *